United States Patent [19]

Imam et al.

[11] Patent Number: 5,258,923
[45] Date of Patent: Nov. 2, 1993

[54] SYSTEM AND METHOD FOR DETECTING THE OCCURRENCE, LOCATION AND DEPTH OF CRACKS IN TURBINE-GENERATOR ROTORS

[75] Inventors: Imdad Imam; Steven H. Azzaro, both of Schenectady; Raymond J. Bankert, Latham, all of N.Y.

[73] Assignee: General Electric Company, New York, N.Y.

[21] Appl. No.: 76,311

[22] Filed: Jul. 22, 1987

[51] Int. Cl.$^5$ .............................. G01M 7/00
[52] U.S. Cl. .................... 364/508; 364/562; 364/582; 73/579; 340/683
[58] Field of Search ............... 364/506-508, 364/550-552, 582, 574; 340/679, 680, 683; 73/570, 579, 593, 598, 600, 602, 658-660; 371/22.4, 25.1

[56] References Cited

U.S. PATENT DOCUMENTS

| | | | |
|---|---|---|---|
| 4,314,347 | 2/1982 | Stokely | 364/574 |
| 4,408,285 | 10/1983 | Sisson et al. | 364/508 |
| 4,408,294 | 10/1983 | Imam | 364/508 |
| 4,426,641 | 1/1984 | Kurihara et al. | 364/508 |
| 4,435,770 | 3/1984 | Shiohata et al. | 364/508 |
| 4,453,407 | 6/1984 | Sato et al. | 364/508 |
| 4,520,674 | 6/1985 | Canada et al. | 364/508 |
| 4,635,210 | 1/1987 | Shiohata et al. | 364/508 |
| 4,685,335 | 8/1987 | Sato et al. | 364/508 |
| 4,751,657 | 6/1988 | Imam et al. | 364/507 |
| 4,782,456 | 11/1988 | Poussier et al. | 364/574 |
| 4,783,998 | 11/1988 | Sander | 364/508 X |
| 4,977,516 | 12/1990 | Shepherd | 73/660 X |

Primary Examiner—Thomas G. Black
Assistant Examiner—Michael Zanelli
Attorney, Agent, or Firm—Flehr, Hohbach, Test, Albritton & Herbert

[57] ABSTRACT

System and method for detecting the occurrence, location and depth of a crack in the rotor of a turbine-generator. The location and depth of a crack are determined by monitoring the fundamental and histogram harmonic components of vibrations at certain predetermined points along the length of the rotor. The histogram harmonic components are normalized relative to the fundamental component, and the normalized histogram harmonic components are monitored to determine the location of the crack. The unnormalized histogram harmonic components are analyzed to determine the depth of the crack. The occurrence of a crack is detected by monitoring the amplitude and phase of rotor vibrations during an accel or decel operation to detect harmonic resonances which are characteristic of a crack in the rotor. The amplitude and phase data is filtered to eliminate spurious data, and it is interpolated to provide baseline and current data at matching speed points.

48 Claims, 9 Drawing Sheets

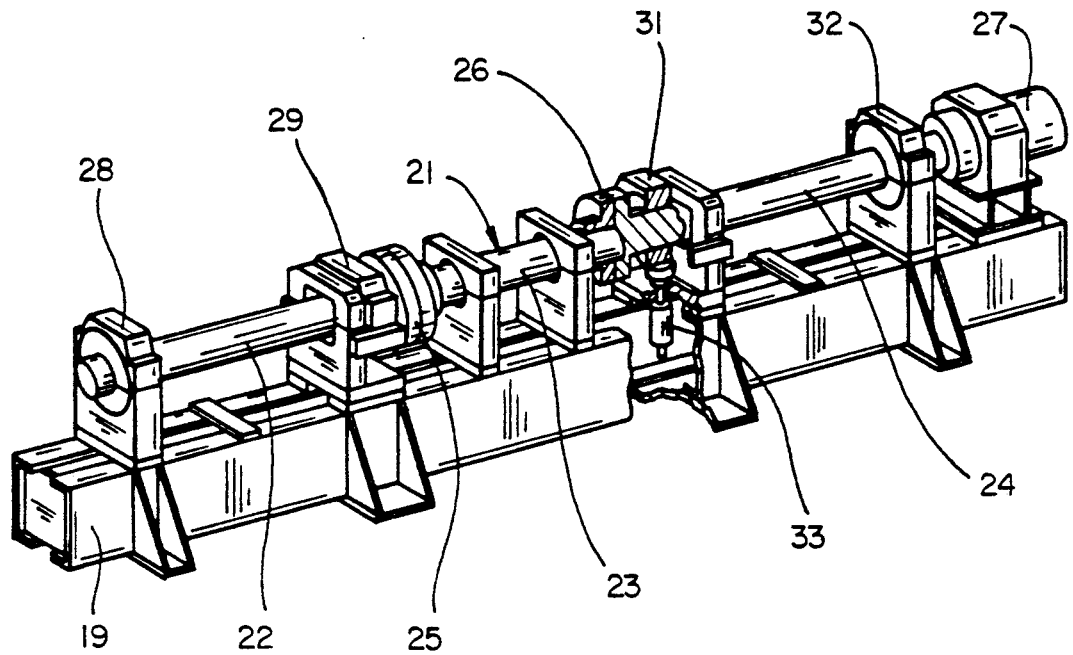
FIG_1
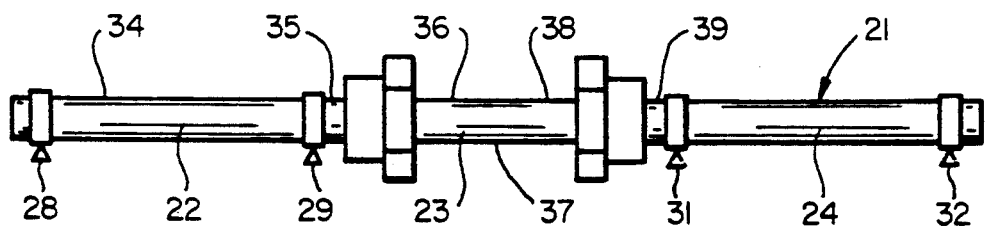
FIG_2

2/REV-HORIZONTAL / CRACK AT POINT 37

| BRNG | 1% | 5% | 10% | 15% | 20% | 25% | 30% |
|---|---|---|---|---|---|---|---|
| 28 | 1.608 | 1.606 | 1.605 | 1.608 | 1.615 | 1.627 | 1.644 |
| 29 | 0.465 | 0.463 | 0.463 | 0.463 | 0.465 | 0.463 | 0.475 |
| 31 | 0.458 | 0.457 | 0.460 | 0.461 | 0.461 | 0.463 | 0.465 |
| 32 | 1.593 | 1.595 | 1.601 | 1.603 | 1.605 | 1.612 | 1.623 |

FIG_3

3/REV-HORIZONTAL / CRACK AT POINT 37

| BRNG | 1% | 5% | 10% | 15% | 20% | 25% | 30% |
|---|---|---|---|---|---|---|---|
| 28 | 1.146 | 1.148 | 1.147 | 1.151 | 1.167 | 1.199 | 1.245 |
| 29 | 0.207 | 0.206 | 0.206 | 0.206 | 0.209 | 0.210 | 0.224 |
| 31 | 0.198 | 0.199 | 0.202 | 0.204 | 0.206 | 0.210 | 0.217 |
| 32 | 1.110 | 1.118 | 1.133 | 1.142 | 1.154 | 1.178 | 1.215 |

FIG_4

2/REV-VERTICAL CRACK AT POINT 38

| BRNG | 10% | 15% | 25% |
|---|---|---|---|
| 28 | 2.006 | 1.961 | 1.887 |
| 29 | 17.684 | 17.174 | 16.439 |
| 31 | 2.663 | 2.635 | 2.535 |
| 32 | 1.012 | 0.997 | 0.961 |

FIG_5

2/REV-VERTICAL CRACK AT POINT 36

| BRNG | 10% | 15% | 25% |
|---|---|---|---|
| 28 | 1.029 | 1.011 | 0.969 |
| 29 | 2.707 | 2.672 | 2.555 |
| 31 | 18.260 | 17.561 | 16.702 |
| 32 | 2.030 | 1.984 | 1.895 |

FIG_6

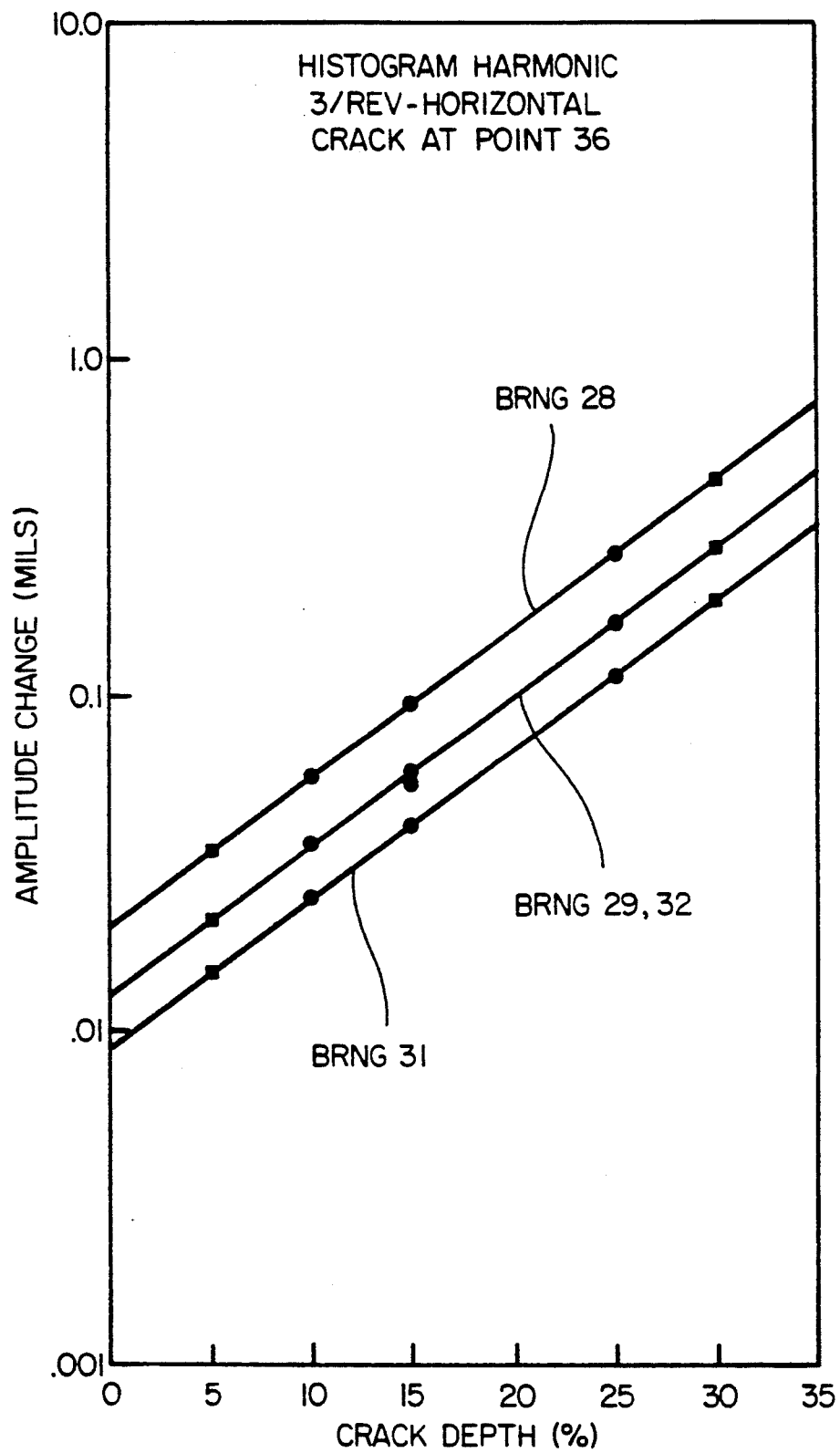
FIG_7

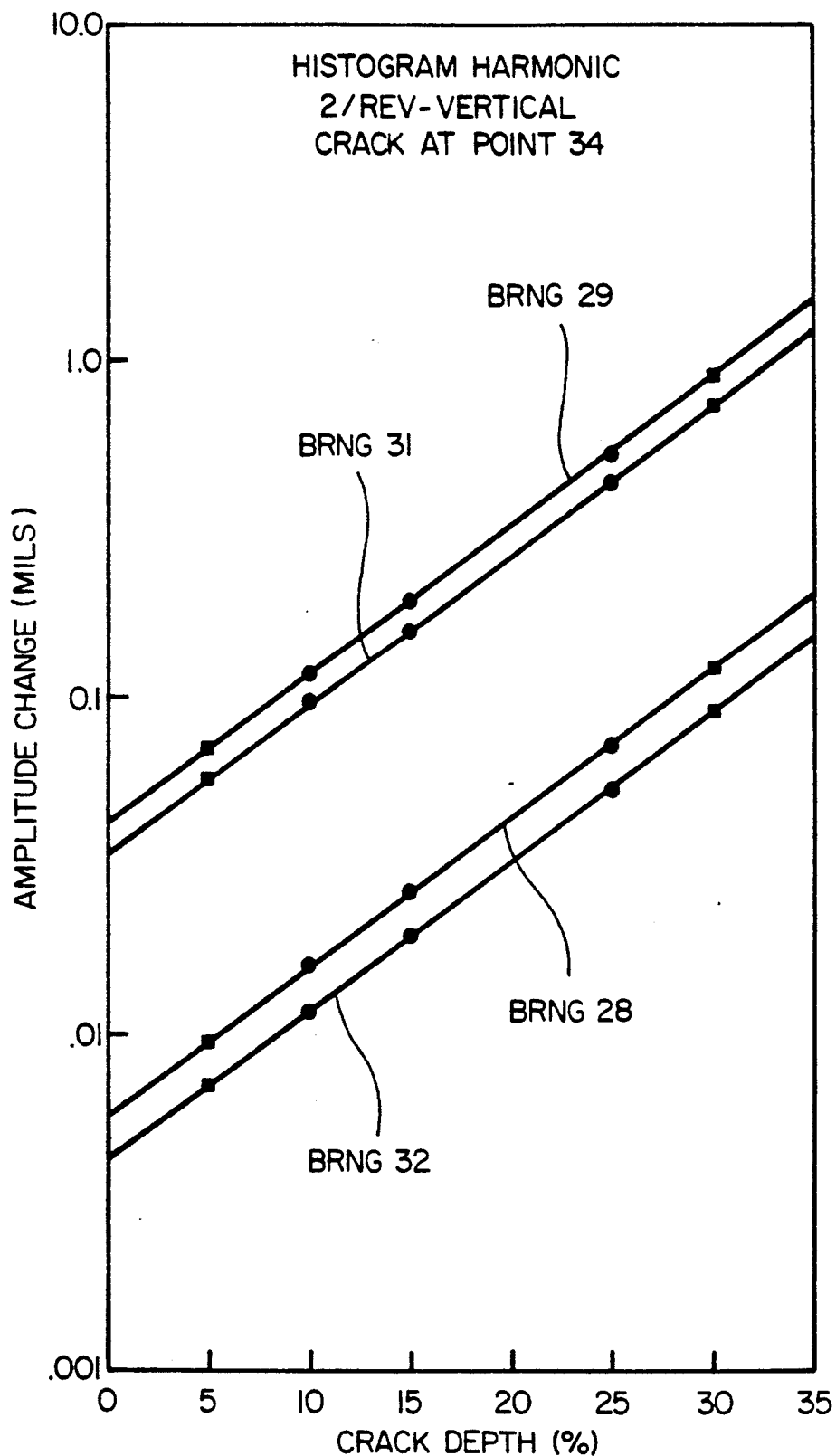
FIG_8

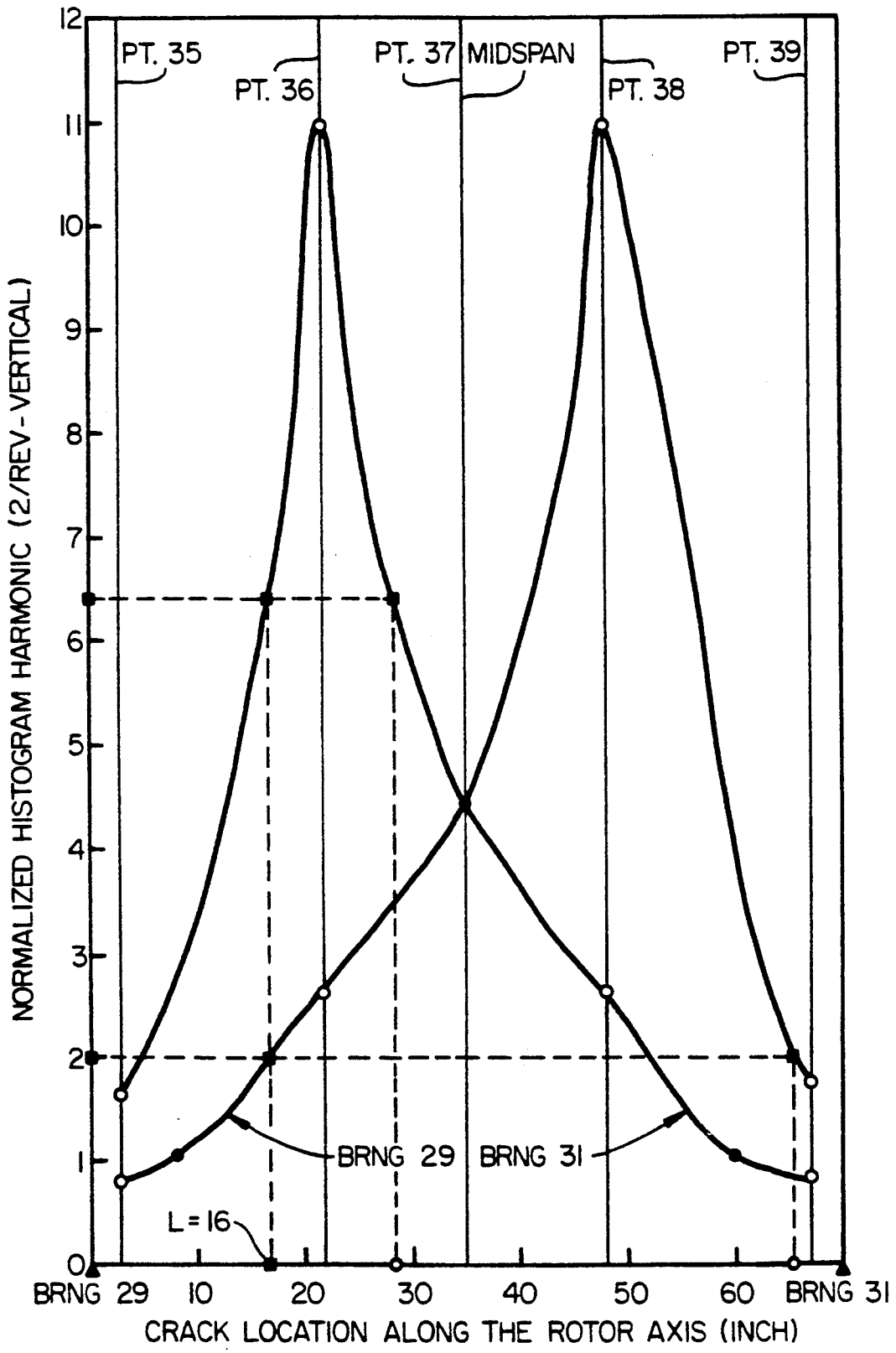
FIG_9

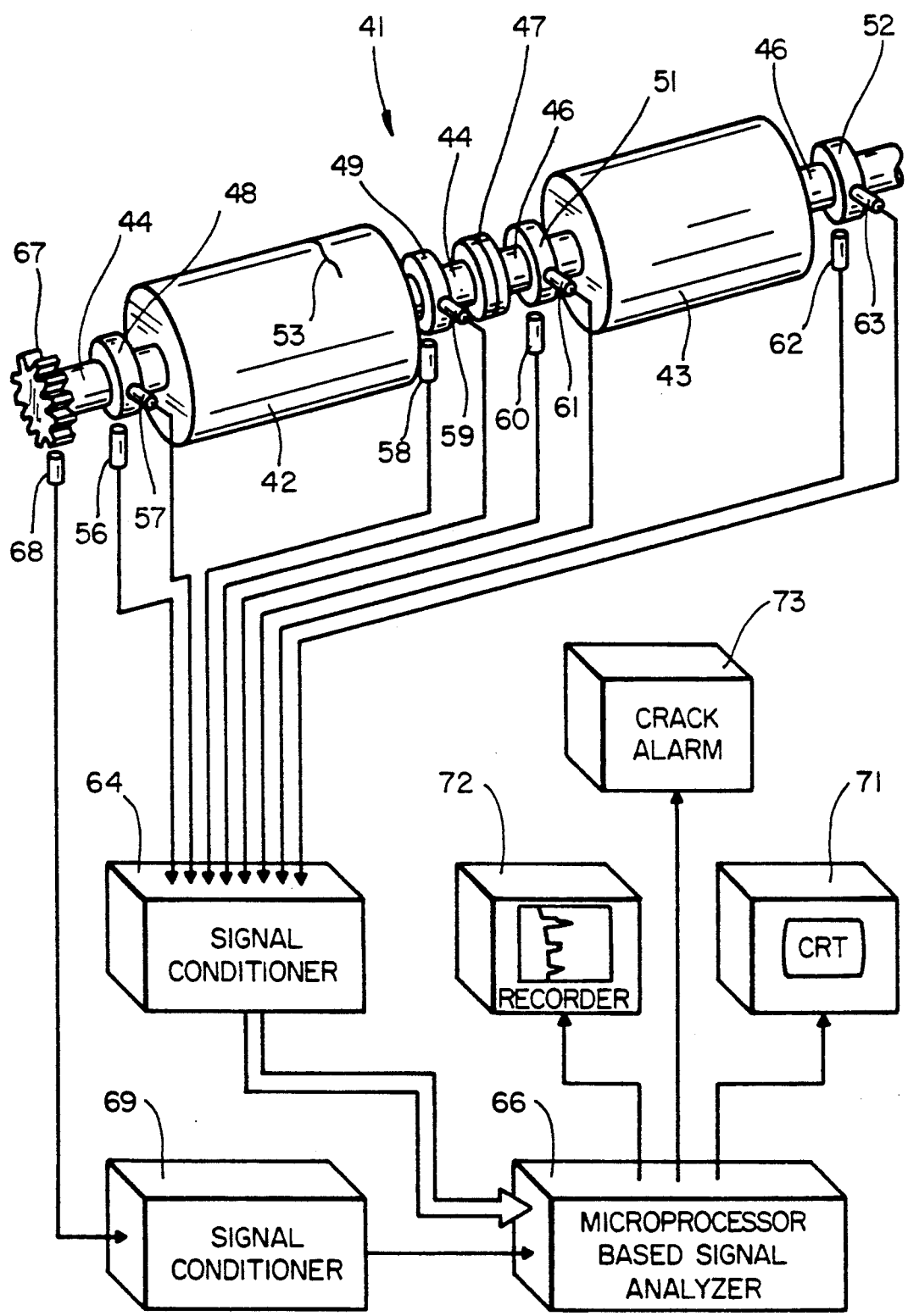
FIG_10

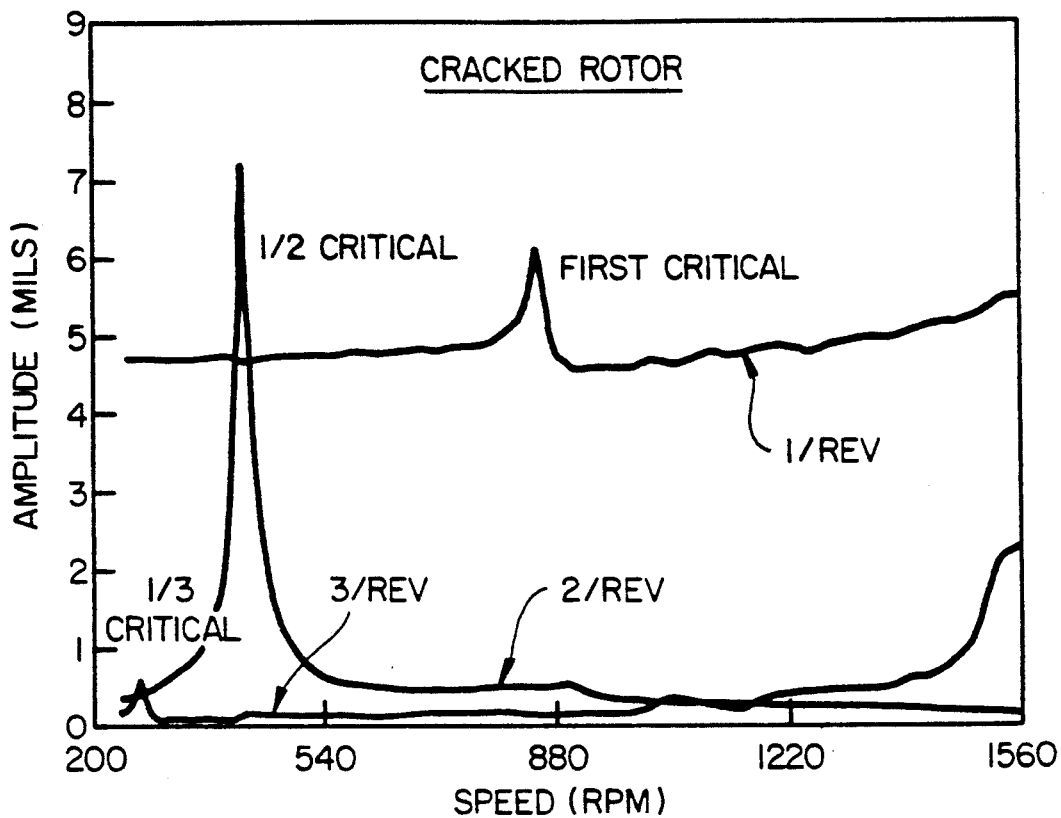
FIG_11
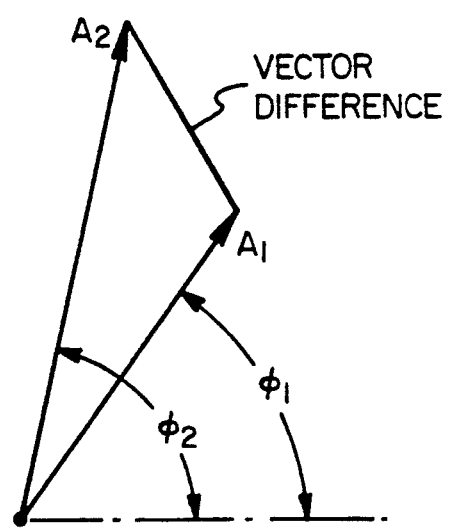
FIG_14

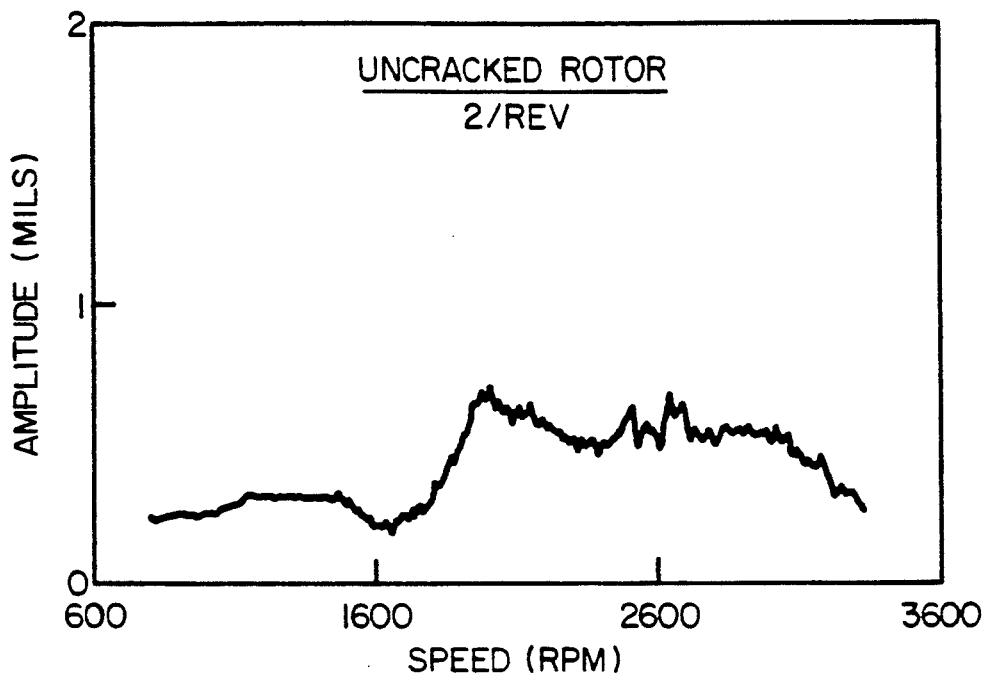
FIG_12
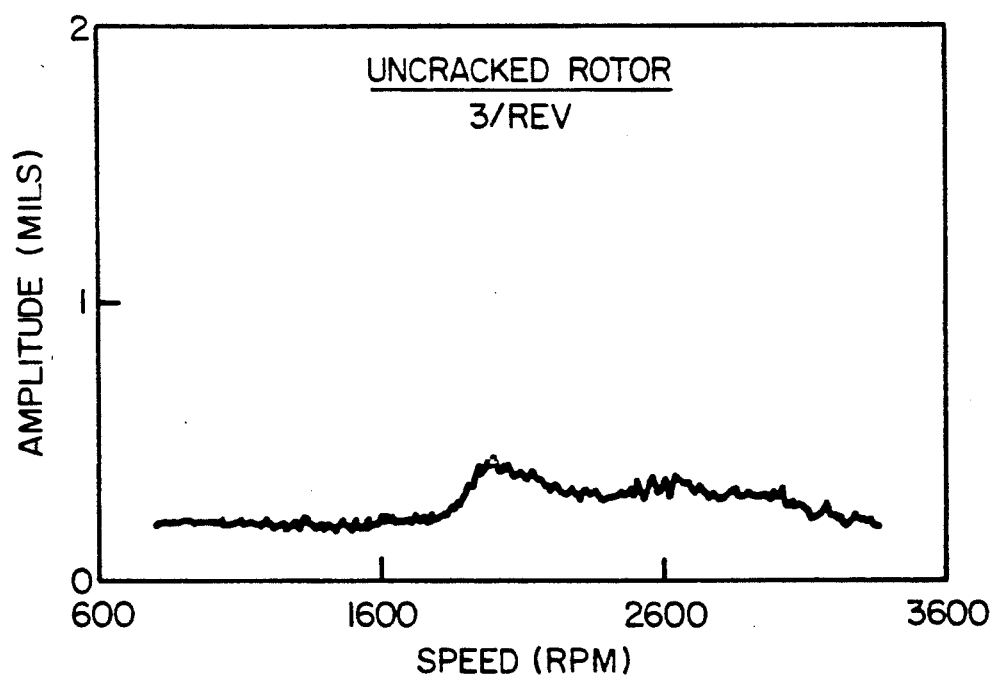
FIG_13

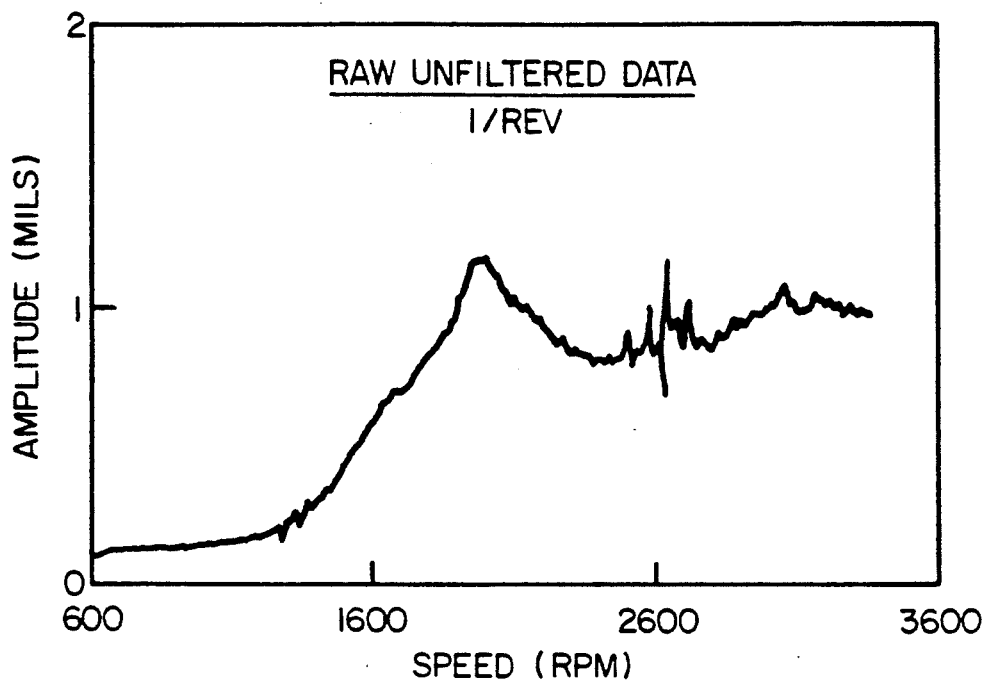
FIG_15
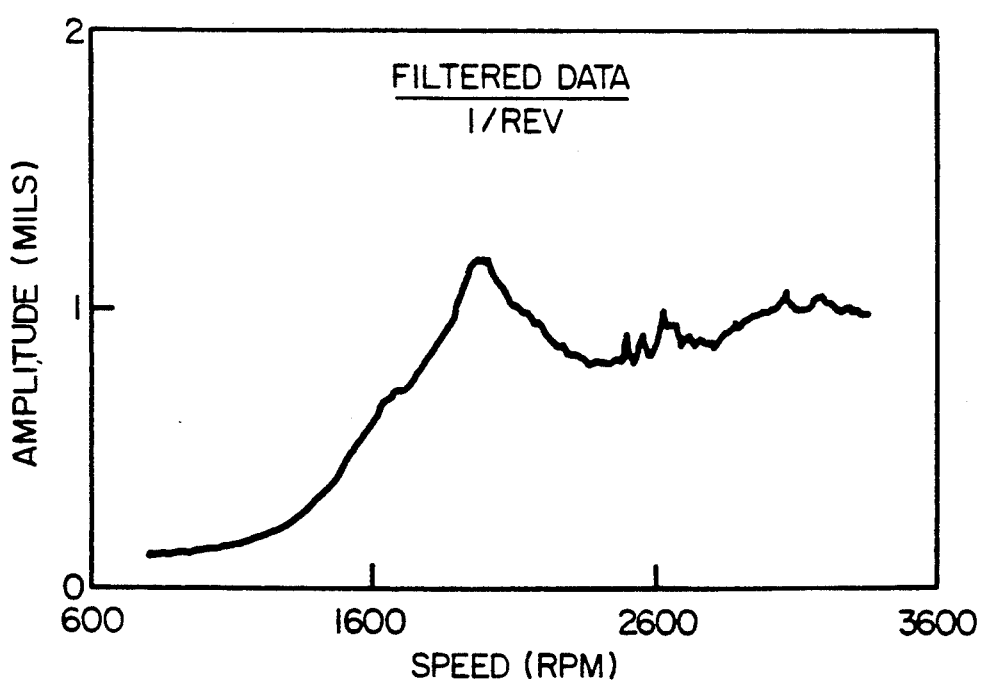
FIG_16

SYSTEM AND METHOD FOR DETECTING THE OCCURRENCE, LOCATION AND DEPTH OF CRACKS IN TURBINE-GENERATOR ROTORS

This invention pertains generally to the detection of cracks in the rotor of a turbine-generator set, and more particularly to a system and method for detecting the occurrence, location and depth of such cracks.

Cracking in the rotor of a turbine-generator such as a large steam driven turbine-generator set of the type used in the commercial generation of electrical power can be a significant problem for an electrical utility company because it can lead to one of the most serious of all plant failures. While the rotor forgings used in large steam turbine units are of the highest quality and are designed for safety and reliability, there have nevertheless been numerous instances of major cracks developing in turbine rotors. In some cases, the rotor has ruptured in a brittle fracture mode. Such failures can have catastrophic results, including massive property damage, serious personal injury, and the loss of life. In other cases, a rotor shaft has failed due to the propagation of a fatigue crack transverse to the axis of rotation of the shaft. With either type of failure, the turbine-generator may be out of service for an extended period of time, and the resulting loss of power generating capacity can be very costly.

If a crack is discovered at an early stage, it may be possible to repair the rotor economically and return it to service in a relatively short period of time. If, however, the crack has grown to the point that the rotor must be replaced, there is not only the relatively high cost of replacement, but also the potentially greater cost resulting from the loss of power generating capacity.

A number of techniques have heretofore been employed to detect the presence and growth of rotor cracks. These include (1) surface inspection methods such as magnetic particle testing, eddy current testing, and dye penetrant techniques; and (2) volumetric methods such as ultrasonic testing (audiography). Unfortunately, none of these techniques is suitable for inspection while the machine is on-line and running underload, and it is necessary to take the machines off-line periodically for testing. Even though a rotor may be sound at the time it is tested, there is a risk that a crack may develop and grow undetected between inspections.

Other techniques based on vibration signature analysis have also been employed for rotor crack detection and have provided some relief from the need to bring the machine to a complete stop. With some of these techniques, it is necessary to take the machine off-line and decelerate it to nearly zero speed to determine if a crack is present. In another of the signature analysis techniques, the rotor is transitorily perturbed while the turbine-generator is operating at normal speed and supplying power to a load so that any crack present will manifest itself by producing a new and different vibration response mode. While this technique does permit incipient cracks to be detected during on-line operation of the machine, it is generally desirable to avoid such perturbations since there is a potential for harmful mechanical or thermal stress on the rotor. Furthermore, since the method is based on a transient response, it does not lend itself to continuous, unattended monitoring.

U.S. Pat. No. 4,408,294 discloses a signature analysis technique in which rotor vibrations are monitored during normal operation of a turbine-generator and the occurrence of a crack is detected primarily by the appearance and increase in the relative amplitude of harmonics at twice the rotational speed of the rotor. With this method, however, it is possible to detect only the occurrence of the crack, not the location or depth of the crack.

It is in general an object of the invention to provide a new and improved system and method for system and method for detecting the occurrence, location and depth in cracks of turbine-generator motors.

Another object of the invention is to provide a system and method of the above character which overcome the limitations and disadvantages of methods heretofore employed for detecting cracks in turbine-generator rotors.

Another object of the invention is to provide a system and method of the above character in which the location and depth of a crack can be determined while the turbine-generator is on-line and operating under normal load.

Another object of the invention is to provide a system and method of the above character which are at least as sensitive as the most sensitive methods heretofore provided for detecting cracks at an early stage.

These and other objects are achieved in accordance with one embodiment of the invention by sensing mechanical vibrations of the rotor at a plurality of predetermined points along the length of the rotor while the turbine-generator is operating at running speed and providing an electrical signal corresponding to the vibration of the rotor at each of the predetermined points. Prior to the development of a crack, the vibration signals produced at each of the predetermined points during a number of revolutions of the rotor are sampled and averaged to provide an enhanced background signal which is stored. The vibration signals produced during normal operations of the turbine-generator are likewise sampled and averaged to provide an enhanced foreground signal for each of the points. The enhanced background signals are subtracted from the enhanced foreground signals, and the spectral content of the difference signals is analyzed to provide fundamental and histogram or differential harmonic components for each of the predetermined points. The differential harmonic components are normalized relative to the fundamental components to provide normalized harmonic signals for the respective points. The normalized differential harmonic signals are monitored to determine the location of a crack relative to the predetermined points, and the unnormalized harmonic components are analyzed to determine the depth of the crack. It has been found that the normalized amplitude of a given harmonic at a given point along the rotor is substantially independent of the crack depth, although it does vary with crack location. It has also been found that when the logarithms of the absolute differential harmonic responses are plotted as a function of crack depth, the slope of the curves is substantially the same for all harmonics at all points along the length of the rotor, varying only as a function of crack depth. Thus, the normalized differential harmonic components contain crack location data, and the unnormalized components contain crack depth data.

In another embodiment, the amplitude and phase of vibrations in the rotor are sensed at different speeds during a change in the speed of the rotor prior to development of a crack to provide baseline amplitude and phase data. The amplitude and phase of the vibrations are also monitored during a subsequent change in the rotor speed to provide current amplitude and phase data. The vectorial difference between harmonic components of the current data and the baseline data is determined, and the vectorial difference is monitored to detect the occurrence of a crack. The data is filtered to remove spurious data points, and the data is interpolated to provide background data and current data at similar rotor speeds.

FIG. 1 is an isometric view of a rotor fatigue test machine utilized in the development of the invention.

FIG. 2 is a schematic view illustrating the formation of cracks at different points along the length of the rotor in the machine of FIG. 1.

FIGS. 3-6 are tables illustrating the relationship between differential harmonic response and crack depth at different points along the rotor in the machine of FIG. 1.

FIGS. 7 and 8 are graphical representations illustrating the relationship between the logarithm of differential harmonic response and crack depth for cracks occurring at different points along the length of the rotor in the machine of FIG. 1.

FIG. 9 is a graphical representation illustrating the relationship between normalized differential harmonic response and crack location at different points along the length of the rotor in the machine of FIG. 1.

FIG. 10 is a simplified schematic diagram of a system for determining the occurrence, location and depth of a crack in a turbine-generator rotor in accordance with the invention.

FIG. 11 is a graphical representation illustrating fundamental and harmonic response as a function of rotor speed during the coast-down (decel) operation of a turbine-generator having a cracked rotor.

FIGS. 12 and 13 are graphical representations of harmonic response as a function of rotor speed during the coast-down (decel) operation of a turbine-generator having an uncracked rotor.

FIG. 14 is a vector diagram illustrating the manner in which the vector difference between current data and baseline data is obtained in accordance with the invention.

FIGS. 15 and 16 are graphical representations of unfiltered and filtered data obtained during the coast-down (decel) operation of a turbine-generator.

A crack in the rotor of a turbine-generator such as a large steam turbine-generator causes the bending stiffness of the rotor to change with the angular position of the rotor, producing a pattern of vibrations which differs from the pattern of vibrations produced by an uncracked rotor rotating at its normal operating speed. An asymmetry in the stiffness of the rotor also appears during an increase or a decrease in the speed of the rotor when a transverse crack is present. Both the vibration patterns of a rotor turning at a steady operating speed and the vibrations which occur during acceleration or deceleration of the rotor are monitored by vibration sensors which detect deflection of the rotor at different points along its length.

The vibration signals are analyzed by a digital computer in accordance with a model prepared to simulate the operation of the machine and the effect of rotor cracks of different location and depth. Such programs have been prepared by the manufacturers of large rotating machines such as turbine-generator sets and are known to persons familiar with the art. The parameters of the program are adjusted to provide a close match between the model and the performance of the machine.

In the test machine of FIG. 1, an elongated bed or base 19 support a test rotor 21. The rotor is formed in three sections 22, 23, 24 which are joined together in axial alignment by couplings 25, 26. A motor 27 is mounted on the base and connected to one end of the rotor for spinning the rotor about its axis. The rotor is rotatively supported by bearings 28, 29, 31, 32 which are spaced along the length of the rotor. A pair of hydraulic actuators 33 are positioned to apply an external moment to the rotor to initiate a crack in the rotor. A pair of vibration sensors (not shown) are provided at each bearing, and the sensors in each pair are positioned to detect deflections of the rotor in horizontal and vertical directions.

In an on-line mode, with the rotor rotating at a normal operating speed, the most important indication of the presence of a crack is given by the initial appearance and/or steady increase in the 1/Rev, 2/Rev, 3/Rev and higher harmonics. The appearance or increase in the 2/Rev harmonic is particularly important because it is a key factor in determining the presence, location and depth of a transverse or circumferential crack.

The tables in FIGS. 3-6 contain normalized "histogram harmonic" data for different crack locations and depths in the test machine of FIG. 1. This data was obtained by making a series of computer runs for cracks at different locations and depths, and processing the vibration signals for each of the bearings in the manner described in U.S. Pat. No. 4,408,294. Briefly, the signal from each of the vibration sensors is sampled a number of times (e.g. 256 samples) during each revolution of the rotor, and the corresponding signals from a number of revolutions (e.g. 500-1,000 revolutions) are averaged together to provide an enhanced background signal. This signal is obtained and stored prior to the development of a crack. Thereafter, the vibration sensor signals are monitored and processed in a similar manner on an ongoing basis to provide an enhanced foreground signal for each of the sensors. The enhanced background signals are superposed with and subtracted from the enhanced foreground signals, and difference signals are analyzed to provide fundamental and harmonic components for each of the sensors. These components are all normalized relative to the 1/Rev component for each of the sensors.

The table of FIG. 3 contains normalized second histogram harmonic data for cracks ranging in depth from 1% to 30% of the rotor diameter at a point 37 midway between inner bearings 29, 31.

The table of FIG. 4 contains the normalized third histogram harmonic data for the same crack depths and location. In each of these cases, the vibrations or deflections are in the horizontal direction.

The tables of FIGS. 5 and 6 contain normalized second histogram harmonic data for cracks ranging in depth from 10% to 25% of the rotor diameter at points 38, 36 on opposite sides of midpoint 37. This data is for vibrations or deflections in the vertical direction.

From the tables of FIGS. 3-6, it will be noted that the normalized second and third histogram harmonics vary in amplitude with the location of the crack. However, somewhat surprisingly, the normalized amplitudes of these harmonics are substantially independent of crack depth. This can be seen by comparing the normalized harmonic responses at each of the bearings for cracks of different depths. Thus, for example, as illustrated in FIG. 3, the normalized second harmonic response at bearing 29 varies only between 0.463 and 0.475 for cracks at point 37 ranging in depth between 1% and 30% of the diameter of the rotor. This result is significant because it means that crack location can be determined from the normalized harmonic data independently of crack depth.

It has also been found that when the natural logarithms of the absolute changes in harmonics (as opposed to the normalized changes discussed above) are plotted as a function of crack depths, the slope of the curve remains substantially the same for responses at all bearings, for all harmonics and in both vertical and horizontal directions. Examples of these results are given in FIGS. 7 and 8. FIG. 7 shows the unnormalized third harmonic responses produced in a horizontal direction at each of the four bearings by cracks of different depths at point 36, and FIG. 8 shows the unnormalized second harmonic responses produced by cracks of different depths at point 34. In the figures, the depth of the crack is plotted on a linear scale along the x-axis, and the unnormalized harmonic response is plotted on a logarithmic on the y-axis. It will be noted that the slope of each of the curves in each figure is the same and that the slopes of the curves in the two figures are also the same. A similar set of curves is prepared for each point along the length of the rotor where a crack might occur, and these curves and/or the data on which they are based is stored.

FIG. 9 shows the normalized second harmonic responses produced at bearings 29 and 31 by cracks located at different points along the rotor axis in the test machine of FIG. 1. In this figure, the normalized harmonic responses are plotted as a function of crack location along the rotor axis in units of distance from bearing 29. This information is determined analytically and stored in the data base for a given machine.

As an example with the test machine, a crack was applied to the rotor at a distance of sixteen inches from bearing 29. This produced second harmonic responses with normalized magnitudes of 2.0 and 6.4 at bearings 29 and 31, respectively. From FIG. 9, it will be noted that the normalized response of 2.0 for the second harmonic at bearing 29 corresponds to crack locations of 16 and 66 inches from bearing 29 and that a normalized second harmonic response of 6.4 at bearing 31 corresponds to crack locations at 16 and 28 inches from bearing 29. The crack location common to the responses at the two bearings is the location 16 inches from bearing 29, where the crack was applied.

Having determined the location of a crack, the depth of the crack is determined from the following relationship $$(Y_i)_n = (P_i)_n e^{b1a - b2}$$

with reference to the curves relating harmonic response and crack depth at that location (e.g. FIGS. 7-8). In this relationship, $(Y_i)_n$ is the unnormalized $n^{th}$ harmonic component measured in a given direction (e.g. horizontal or vertical) at a point i along the length of the rotor. Point i can be any point where a sensor is located, and in the test machine of FIG. 1, it is at one of the bearings. $(P_i)_n$ is the unnormalized $n^{th}$ harmonic component of a vibration at point i produced by a crack of the smallest depth to be determined. For a crack at point 36 in the rotor of the test machine, for example, the third harmonic value of $(P_i)_n$ in the horizontal direction is equal to the y-value of the curve for the bearing where the measurement is made for a crack depth of 5%. $(P_i)_n$ is taken in the same direction as $(Y_i)_n$, e.g. horizontal or vertical.

In the relationship for determining the depth of the crack, e is the logarithmic exponential, $b_1$ and $b_2$ are constants which define the slope of the curves plotting the logarithm of the unnormalized components as a function of crack depth, and a is the depth of the crack expressed as a percentage of the rotor diameter. The constants $b_1$ and $b_2$ define the slope of the curves in FIGS. 7 and 8, and they are calculated from the following relationship:

$$\log y(a) - \log y(5\%) = \left( \frac{\log y(25\%) - \log y(5\%)}{25\% - 5\%} \right)(a - 5\%)$$

where log y of (a) is the y-value at crack depth a, log y of 5% is the y-value at a crack depth of 5% and log y(25%) is the y-value at a crack depth of 25%. Solving this equation for y gives $y = Y(5\%)e^{0.109a - 0.542}$. From this expression, it can be seen that $b_1 = 0.109$ and $b_2 = 0.542$ for the test machine of FIG. 1.

The relationship $(Y_i)_n = (P_i)_n e^{b1a - b2}$ may give slightly different values for the crack depth a for different harmonics and vibrations at different points in a given machine, depending on how closely the model is matched to the machine. It is therefore desirable to calculate the value of a for both the second harmonic and the third harmonic in both horizontal and vertical directions at different points along the rotor, and then average the most consistent values of a to determine the crack depth.

In the relationship $(Y_i)_n = (P_i)_n e^{b1a - b2}$, it is significant that the expression $(P_i)_n$ contains only crack location information and the expression $e^{b1a - b2}$ contains only crack depth of the information. $(P_i)_n$ is independent of crack depth, and $e^{b2a - b2}$ is the same for all crack locations and all bearings in both vertical and horizontal directions for a given machine. This makes it possible to determine the location of a crack and the depth of a crack independently of each other.

FIG. 10 schematically illustrates the hardware in one embodiment of a system for analyzing the signals produced by vibrations in the rotor 41 of a turbine in accordance with the invention. The hardware itself is similar to the hardware disclosed in U.S. Pat. No. 4,408,294, although the signals are analyzed and processed differently in the two systems. Rotor 41 has a pair of rotor wheels 42, 43 which carry a plurality of radially extending buckets or blades (not shown). Rotor wheels 42, 43 are mounted on shafts 44, 46 which are connected together by a coupling 47 for rotation as a unit in bearings 48, 49, 51 and 52. For purposes of explanation, an illustrative crack 53 is shown on the surface of rotor wheel 42.

Vibrations in rotor 41 are detected by vibration sensors 56-63 which are arranged in orthogonal pairs of four monitoring the horizontal and vertical components of vibrations at the bearings. The electrical output signals from the sensors are processed by a signal conditioner 64 and applied to a microprocessor-based signal analyzer 66.

The angular position of rotor 41 is monitored by a toothed wheel 67 mounted on shaft 44 and a magnetic pickup 68. The signal from the magnetic pickup is processed by a signal conditioner 69 and applied to signal analyzer 66 to provide correlation between the position of the rotor and the signals from sensors 56-63.

The signals from vibration sensors 56-63 are processed by analyzer 66 in the manner hereinbefore described to determine the location and depth of a crack and in the manner hereinafter described to determine the presence of an incipient crack. The analyzer or computer is capable of handling each vibration signal separately, although with high-speed signal processing techniques currently available, each signal is analyzed essentially concurrently on a virtual real-time basis.

Suitable output devices such as a cathode ray tube (CRT) monitor and a graphic recorder 72 are connected to the signal analyzer to display and record the information from the analyzer. An alarm 73 is also connected to the output of the analyzer to provide an audible and/or visible indication when a crack is detected.

The hardware illustrated in FIG. 10 can be utilized to determine the location and depth of a crack in the rotor of a turbine-generator while it is operating in an on-line mode. It can also be utilized to detect the presence of an incipient crack during acceleration or deceleration of the rotor.

During a speed change operation (either run-down or run-up) of a turbine-generator, if a transverse crack is present in the rotor system, additional frequencies appear in the vibration response spectrum. These additional frequencies include the second and third resonance harmonics which appear at one-half and one-third of the first critical speed, respectively. FIG. 11 illustrates the decel spectrum for a cracked rotor system monitored at a single point along the length of the rotor. The first critical speed as the rotor is decelerated is at 860 rpm, as indicated by the peak in the fundamental (1/Rev) signal. A resonance occurs in the second harmonic component (2/Rev) at a speed of 430 rpm, which is one-half the first critical speed, and a resonance occurs in the third harmonic component (3/Rev) at a speed of 287 rpm, which is one-third the first critical speed. These resonances are indications of asymmetry in the stiffness of the rotor. When there is no crack in the system, the 2/Rev and 3/Rev resonance harmonics do not appear in the decel or accel spectrum, as can be seen from FIGS. 12 and 13. These figures show the second and third harmonic components during the deceleration of an uncracked rotor, and these components are free of the resonances which occur at one-half and one-third of the critical speed with a cracked rotor. By detecting the harmonic resonances, it is possible to detect the presence of a crack when it is still relatively small.

In order to detect the presence of the harmonic resonances which indicate the presence of a crack, both the amplitude and the phase of vibrations in the rotor are sampled at as many speed points as possible during a run-down or run-up operation. This data is collected initially when the machine is first put in operation or is otherwise known to be free of cracks in order to provide baseline or background data. The baseline data is stored, and current amplitude and phase data is collected during subsequent decel or accel operations. For both the baseline data and the current data, the amplitude and phase data for the second and third harmonics is collected synchronously, using the fundamental or 1/Rev component as a reference signal. The vector difference is then taken between the current data and the baseline data, and illustrated in FIG. 14. The subtraction is done on a harmonic by harmonic basis and is performed vectorially for each speed point in the baseline data. The resulting differential harmonics can be referred to as decel or accel histogram resonance harmonics of 2/Rev and 3/Rev at one-half and one-third of the critical speed, respectively. These harmonics contain only crack information and are very sensitive in detecting a transverse crack in a turbine-generator rotor.

During a decel operation, or an accel operation, the system changes very fast on a dynamic basis, and on-line data collection is very difficult. It has been found to be helpful to do some filtering of the data to remove spurious data points. In the paragraphs which follow, the filtering process is described with specific reference to a decel operation, but it will be understood that these same techniques can be employed in an accel operation.

During a coast-down or decel operation, the speed of a turbine-generator set decreases smoothly, and a keyphasor signal is monitored to indicate the speed of the rotor. If this signal suddenly increases in frequency or drops by more than 100 rpm between successive data collection, the data is disregarded.

The phase data is checked by comparing the phase data for each speed point with the phase data for the previous speed point for the 1/Rev, 2/Rev and 3/Rev harmonics. If a large excursion is found in all three cases, the data for the current point is ignored.

The amplitude data is checked by computing the slope of the amplitude data between every two adjacent data points by dividing the difference in amplitude by the difference in speed between the two points. If an extraordinary change exists for either the 1/Rev, the 2/Rev or the 3/Rev harmonic, the data for the later point is ignored.

The effectiveness of this filtering process can be seen by comparing the raw unfiltered 1/Rev data of FIG. 15 with the filtered data of FIG. 16. In this example, spurious responses at approximately 1300 rpm and 2600 rpm have been substantially reduced or eliminated.

The speeds at which data is collected on a current basis may differ from the speeds at which the baseline data is collected due to the rapidly changing dynamics of an accelerating or decelerating rotor system. To match the speed points for the current data with the speed points for the baseline data, the current data is interpolated using a least squared fit technique is employed. In this technique, the amplitude and phase data is stepped through on a point by point basis, taking two adjacent points ahead of the desired point and two points behind the desired point and fitting a quadratic least squared fit through these five points:

$$\text{Amplitude} = a_0 + a_1 x + a_2 x^2$$

$$\text{Phase} = b_0 + b_1 x + b_2 x^2$$

This interpolation makes it possible to match the speeds almost exactly for the baseline data and the current data.

It is apparent from the foregoing that a new and improved system and method for detecting the occurrence, location and depth of a crack in the rotor of a turbine-generator. While only certain presently preferred embodiments have been described in detail, as will be apparent to those familiar with the art, certain changes and modifications can be made without departing from the scope of the invention as defined by the following claims.

I claim:

1. A system for determining the location and depth of a transverse crack along the length of a turbine-generator rotor, comprising means for sensing mechanical vibrations of the rotor at a plurality of predetermined points along the length of the rotor while the turbine-generator is operating at running speed and providing electrical signals having a spectral content corresponding to the vibration of the rotor at each of the predetermined points, means for analyzing the spectral content of the electrical signals to provide fundamental and unnormalized histogram harmonic components for each of the predetermined points, means for normalizing the histogram harmonic components relative to the fundamental components to provide normalized histogram harmonic signals in addition to the unnormalized histogram harmonic components for the respective points, means for monitoring the normalized harmonic signals to determine the location of a crack along the length of the rotor relative to the predetermined points, and means for analyzing the unnormalized histogram harmonic components to determine the depth of the crack as a function of the logarithm of the unnormalized histogram harmonic components.

2. The system of claim 1 wherein the means for monitoring the normalized histogram harmonic signals includes a computer programmed to determine the location of a crack from the normalized second histogram harmonic signals at two points along the length of the rotor.

3. The system of claim 1 wherein the means for analyzing the unnormalized histogram harmonic components includes means for determining the depth of the crack according to the relationship:

$$(Y_i)_n = (P_i)_n e^{b_1 a - b_2}$$

where $(Y_i)_n$ is the unnormalized $n^{th}$ histogram harmonic component measured at point i, $(P_i)_n$ is the unnormalized $n^{th}$ histogram harmonic component of a vibration at point i produced by a crack of predetermined depth, e is the logarithmic exponential, $b_1$ and $b_2$ are constants which define the slope of a curve plotting the unnormalized histogram harmonic component as a function of crack depth, and a is the depth of the crack.

4. A method of determining the location and depth of a transverse crack along the length of a turbine-generator rotor, comprising the steps of sensing mechanical vibrations of the rotor at a plurality of predetermined points along the length of the rotor while the turbine-generator is operating at running speed and providing electrical signals having a spectral content corresponding to the vibration of the rotor at each of the predetermined points, analyzing the spectral content of the electrical signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram harmonic components.

5. The method of claim 4 wherein a computer is programmed to determine the location of a crack from the normalized second histogram harmonic signals at two points along the length of the rotor.

6. A method of determining the location and depth of a transverse crack along the length of a turbine-generator rotor, comprising the steps of sensing mechanical vibrations of the rotor at a plurality of predetermined points along the length of the rotor while the turbine-generator is operating at running speed and providing electrical signals having a spectral content corresponding to the vibration of the rotor at each of the predetermined points, analyzing the spectral content of the electrical signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram harmonic components according to the relationship:

$$(Y_i)_n = (P_i)_n e^{b_1 a - b_2}$$

where $(Y_i)_n$ is the unnormalized $n^{th}$ histogram harmonic component measured at point i, $(P_i)_n$ is the unnormalized $n^{th}$ histogram harmonic component of a vibration at point i produced by a crack of predetermined depth, e is the logarithmic exponential, $b_1$ and $b_2$ are constants which define the slope of a curve plotting the unnormalized histogram harmonic component as a function of crack depth, and a is the depth of the crack.

7. A system for determining the location and depth of a transverse crack along the length of a turbine-generator rotor while the turbine-generator is operating at running speed, comprising means for sensing vibrations at a plurality of predetermined points along the length of the rotor to provide vibration signals having a spectral content corresponding to the vibrations at respective ones of the predetermined points, means for sampling the vibration signals prior to development of a crack to provide a background signal for each of the predetermined points, means for monitoring the vibration signals as the turbine-generator operates to provide a foreground signal for each of the predetermined points, means for subtracting the background signals from the foreground signals to provide a difference signal for each of the predetermined points, means for analyzing the spectral content of the difference signals to provide fundamental and unnormalized histogram harmonic components for each of the predetermined points, means for normalizing the histogram harmonic components relative to the fundamental components to provide normalized histogram harmonic signals in addition to the unnormalized histogram harmonic components for the respective points, means for monitoring the normalized histogram harmonic signals to determine the location of a crack along the length of the rotor relative to the predetermined points, and means for analyzing the unnormalized histogram harmonic components to determine the depth of the crack as a function of the logarithm of the unnormalized histogram harmonic components.

8. The system of claim 7 wherein the means for monitoring the normalized histogram harmonic signals includes a computer programmed to determine the location of a crack form the normalized second histogram harmonic signals at two points along the length of the rotor.

9. A system for determining the location and depth of a transverse crack along the length of a turbine-generator rotor while the turbine-generator is operating at running speed, comprising means for sensing vibration at a plurality of predetermined points along the length of the rotor to provide vibration signals having a spectral content corresponding to the vibrations at respective ones of the predetermined points, means for sampling the vibration signals prior to development of a crack to provide a background signal for each of the predetermined points, means for monitoring the vibration signals as the turbine-generator operates to provide a foreground signal for each of the predetermined points, means for subtracting the background signals from the foreground signals to provide a difference signal for each of the predetermined points, means for analyzing the spectral content of the difference signals to provide fundamental and unnormalized histogram harmonic components for each of the predetermined points, means for normalizing the histogram harmonic components relative to the fundamental components to provide normalized histogram harmonic signals in addition to the unnormalized histogram harmonic components for the respective points, means for monitoring the normalized histogram harmonic signals to determine the location of a crack along the length of the rotor relative to the predetermined points, and means for analyzing the unnormalized histogram harmonic components to determine the depth of the crack as a function of the logarithm of the unnormalized histogram harmonic components according to the relationship:

$$(Y_i)_n = (P_i)_n e^{b_1 a - b_2}$$

where $(Y_i)_n$ is the unnormalized $n^{th}$ histogram harmonic component measured at point i, $(P_i)_n$ is the unnormalized $n^{th}$ histogram harmonic component of a vibration at point i produced by a crack of predetermined depth, e is the logarithmic exponential, $b_1$ and $b_2$ are constants which define the slope of a curve plotting the unnormalized histogram harmonic component as a function of crack depth, and a is the depth of the crack.

10. A method of determining the location and depth of a transverse crack along the length of a turbine-generator rotor while the turbine-generator is operating at running speed, comprising the steps of sensing vibration at a plurality of predetermined points along the length of the rotor to provide vibration signals having a spectral content corresponding to the vibrations at respective ones of the predetermined points, sampling the vibration signals prior to development of a crack to provide a background signal for each of the predetermined points and for monitoring the vibration signals as the turbine-generator operates to provide a foreground signal for each of the predetermined points, subtracting the background signals from the foreground signals to provide a difference signal for each of the predetermined points, analyzing the spectral content of the difference signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram harmonic components.

11. The method of claim 10 wherein a computer is programmed to determine the location of a crack from the normalized second histogram harmonic signals at two points along the length of the rotor.

12. A method of determining the location and depth of a transverse crack along the length of a turbine-generator rotor while the turbine-generator is operating at running speed, comprising means for sensing vibration at a plurality of predetermined points along the length of the rotor to provide vibration signals having a spectral content corresponding to the vibrations at respective ones of the predetermined points, sampling the vibration signals prior to development of a crack to provide a background signal for each of the predetermined points and for monitoring the vibration signals as the turbine-generator operates to provide a foreground signal for each of the predetermined points, subtracting the background signals from the foreground signals to provide a difference signal for each of the predetermined points, analyzing the spectral content of the difference signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram harmonic components according to the relationship:

$$(Y_i)_n = (P_i)_n e^{b_1 a - b_2}$$

where $(Y_i)_n$ is the unnormalized $n^{th}$ histogram harmonic component measured at point i, $(P_i)_n$ is the unnormalized $n^{th}$ histogram harmonic component of a vibration at point i produced by a crack of predetermined depth, e is the logarithmic exponential, $b_1$ and $b_2$ are constants which define the slope of a curve plotting the unnormalized histogram harmonic component as a function of crack depth, and a is the depth of the crack.

13. A system for determining the location and depth of a transverse crack along the length of a turbine-generator rotor while the turbine-generator is operating at running speed, comprising means for sensing vibration at a plurality of predetermined points along the length of the rotor to provide vibration signals having a spectral content corresponding to the vibrations at respective ones of the predetermined points, means for taking a predetermined number of samples of the vibration signal at each of the predetermined points for a plurality of revolutions of the rotor prior to development of a crack, means for combining the samples to provide an enhanced background signal for each of the predetermined points, means for taking the same predetermined number of samples of the vibration signal at each of the predetermined points during normal operation of the turbine-generator, means for combining the samples taken during normal operation to provide an enhanced foreground signal for each of the predetermined points, means for subtracting the background signals from the foreground signals to provide a difference signal for each of the predetermined points, means for analyzing the spectral content of the difference signals to provide fundamental and unnormalized histogram harmonic components for each of the predetermined points, means for normalizing the histogram harmonic components relative to the fundamental components to provide normalized histogram harmonic signals in addition to the unnormalized histogram harmonic components for the respective points, means for monitoring the normalized histogram harmonic signals to determine the location of a crack along the length of the rotor relative to the predetermined points, and means for analyzing the unnormalized histogram harmonic components to determine the depth of the crack as a function of the logarithm of the unnormalized histogram components.

14. The system of claim 13 wherein the means for monitoring the normalized histogram harmonic signals includes a computer programmed to determine the location of a crack from the normalized second histogram harmonic signals at two points along the length of the rotor.

15. A system for determining the location and depth of a transverse crack along the length of a turbine-generator rotor while the turbine-generator is operating at running speed, comprising means for sensing vibration at a plurality of predetermined points along the length of the rotor to provide vibration signals having a spectral content corresponding to the vibrations at respective ones of the predetermined points, means for taking a predetermined number of samples of the vibration signal at each of the predetermined points for a plurality of revolutions of the rotor prior to development of a crack, means for combining the samples to provide an enhanced background signal for each of the predetermined points, means for taking the same predetermined number of samples of the vibration signal at each of the predetermined points during normal operation of the turbine-generator, means for combining the samples taken during normal operation to provide an enhanced foreground signal for each of the predetermined points, means for subtracting the background signals from the foreground signals to provide a difference signal for each of the predetermined points, means for analyzing the spectral content of the difference signals to provide fundamental and unnormalized histogram harmonic components for each of the predetermined points, means for normalizing the histogram harmonic components relative to the fundamental components to provide normalized histogram harmonic signals in addition to the unnormalized histogram harmonic components for the respective points, means for monitoring the normalized histogram harmonic signals to determine the location of a crack along the length of the rotor relative to the predetermined points, and means for analyzing the unnormalized histogram harmonic components to determine the depth of the crack as a function of the logarithm of the unnormalized histogram components.

16. A system for determining the location and depth of a transverse crack along the length of a turbine-generator rotor while the turbine-generator is operating at running speed, comprising means for sensing vibration at a plurality of predetermined points along the length of the rotor to provide vibration signals having a spectral content corresponding to the vibrations at respective ones of the predetermined points, means for taking a predetermined number of samples of the vibration signal at each of the predetermined points for a plurality of revolutions of the rotor prior to development of a crack, means for combining the samples to provide an enhanced background signal for each of the predetermined points, means for taking the same predetermined number of samples of the vibration signal at each of the predetermined points during normal operation of the turbine-generator, means for combining the samples taken during normal operation to provide an enhanced foreground signal for each of the predetermined points, means for subtracting the background signals from the foreground signals to provide a difference signal for each of the predetermined points, means for analyzing the spectral content of the difference signals to provide fundamental and unnormalized histogram harmonic components for each of the predetermined points, means for normalizing the histogram harmonic components relative to the fundamental components to provide normalized histogram harmonic signals in addition to the unnormalized histogram harmonic components for the respective points, means for monitoring the normalized histogram harmonic signals to determine the location of a crack along the length of the rotor relative to the predetermined points, and means for analyzing the unnormalized histogram harmonic components to determine the depth of the crack as a function of the logarithm of the unnormalized histogram harmonic components according to the relationship:

$$(Y_i)_n = (P_i)_n e^{b_1 a - b_2}$$

where $(Y_i)_n$ is the unnormalized $n^{th}$ histogram harmonic component measured at point i, $(P_i)_n$ is the unnormalized $n^{th}$ histogram harmonic component of a vibration at point i produced by a crack of predetermined depth, e is the logarithmic exponential, $b_1$ and $b_2$ are constants which define the slope of a curve plotting the unnormalized histogram harmonic component as a function of crack depth, and a is the depth of the crack.

17. A method of determining the location and depth of a transverse crack along the length of a turbine-generator rotor while the turbine-generator is operating at running speed, comprising means for sensing vibration at a plurality of predetermined points along the length of the rotor to provide vibration signals having a spectral content corresponding to the vibrations at respective ones of the predetermined points, taking a predetermined number of samples of the vibration signal at each of the predetermined points for a plurality of revolutions of the rotor prior to development of a crack, combining the samples to provide an enhanced background signal for each of the predetermined points, taking the same predetermined number of samples of the vibration signal at each of the predetermined points during normal operation of the turbine-generator, combining the samples taken during normal operation to provide an enhanced foreground signal for each of the predetermined points, subtracting the background signals from the foreground signals to provide a difference signal for each of the predetermined points, analyzing the spectral content of the difference signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram components.

18. The method of claim 17 wherein a computer is programmed to determine the location of a crack from the normalized second histogram harmonic signals at two points along the length of the rotor.

19. A method of determining the location and depth of a transverse crack along the length of a turbine-generator rotor while the turbine-generator is operating at running speed, comprising the steps of sensing vibrations at a plurality of predetermined points along the length of the rotor to provide vibration signals having a spectral content corresponding to the vibrations at respective ones of the predetermined points, taking a predetermined number of samples of the vibration signal at each of the predetermined points for a plurality of revolutions of the rotor prior to development of a crack, combining the samples to provide an enhanced background signal for each of the predetermined points, taking the same predetermined number of samples of the vibration signal at each of the predetermined points during normal operation of the turbine-generator, combining the samples taken during normal operation to provide an enhanced foreground signal for each of the predetermined points, subtracting the background signals from the foreground signals to provide a difference signal for each of the predetermined points, analyzing the spectral content of the difference signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram components.

20. A method of determining the location and depth of a transverse crack along the length of a turbine-generator rotor while the turbine-generator is operating at running speed, comprising the steps of sensing vibrations at a plurality of predetermined points along the length of the rotor to provide vibration signals having a spectral content corresponding to the vibrations at respective ones of the predetermined points, taking a predetermined number of samples of the vibration signal at each of the predetermined points for a plurality of revolutions of the rotor prior to development of a crack, combining the samples to provide an enhanced background signal for each of the predetermined points, taking the same predetermined number of samples of the vibration signal at each of the predetermined points during normal operation of the turbine-generator, combining the samples taken during normal operation to provide an enhanced foreground signal for each of the predetermined points, subtracting the background signals from the foreground signals to provide a difference signal for each of the predetermined points, analyzing the spectral content of the difference signals to provide fundamental and unnormalized histogram harmonic components for each of the predetermined points, normalizing the histogram harmonic components relative to the fundamental components to provide normalized histogram harmonic signals in addition to the unnormalized histogram harmonic components for the respective points, monitoring the normalized histogram harmonic signals to determine the location of a crack along the length of the rotor relative to the predetermined points, and analyzing the unnormalized histogram harmonic components to determine the depth of the crack as a function of the logarithm of the unnormalized histogram harmonic components according to the relationship:

$$(Y_i)_n = (P_i)_n e^{b_1 a - b_2}$$

where $(Y_i)_n$ is the unnormalized $n^{th}$ histogram harmonic component measured at point i, $(P_i)_n$ is the unnormalized $n^{th}$ histogram harmonic component of a vibration at point i produced by a crack of predetermined depth, e is the logarithmic exponential, $b_1$ and $b_2$ are constants which define the slope of a curve plotting the unnormalized histogram harmonic component as a function of crack depth, and a is the depth of the crack.

21. A system for detecting an occurrence of a transverse crack in a rotor of a turbine-generator, comprising means for sensing the amplitude and phase of vibrations in the rotor at different speeds during a change in the speed of the rotor prior to development of a crack to provide baseline amplitude and phase data, means for monitoring the amplitude and phase of the vibrations at different speeds during a subsequent change in the rotor speed to provide current amplitude and phase data, means for taking a vector difference between the current data and the baseline data, and means for monitoring the vector difference to detect the occurrence of a crack.

22. The system of claim 21 wherein the means for sensing the amplitude and phase of vibrations to provide baseline data and the means for monitoring the amplitude and phase of the vibrations to provide current data each include means for providing fundamental and harmonic components, the vector differences of the harmonic components being monitored to detect the occurrence of a crack.

23. The system of claim 21 including means for filtering the baseline data and the current data by discarding data which differs from preceding data by more than a predetermined amount.

24. The system of claim 23 wherein the means for filtering the baseline data and the current data includes means for discarding both the amplitude data and the phase data for a data point if the phase data changes by more than a predetermined amount between successive data points or if the amplitude data changes by more than a predetermined amount relative to the speed data between successive data points.

25. The system of claim 23 wherein the means for filtering the baseline data and the current data further includes means for discarding data if the rotor speed changes by more than a predetermined amount between successive data points.

26. The system of claim 21 including means for interpolating the current data to provide current data and baseline data at matching rotor speeds.

27. The system of claim 26 wherein the means for interpolating the data includes means for determining a quadratic least squares fit between successive data points of the current data.

28. A method of detecting an occurrence of a transverse crack in a rotor of a turbine-generator, comprising the steps of: sensing the amplitude and phase of vibrations in the rotor at different speeds during a change in the speed of the rotor prior to development of a crack to provide baseline amplitude and phase data, monitoring the amplitude and phase of the vibrations at different speeds during a subsequent change in the rotor speed to provide current amplitude and phase data, taking a vector difference between the current data and the baseline data, and monitoring the vector difference to detect the occurrence of a crack.

29. The method of claim 28 wherein harmonic components of the baseline data and the current data are monitored to detect the occurrence of the crack.

30. The method of claim 28 including the steps of filtering the baseline data and the current data by discarding data which differs from preceding data by more than a predetermined amount.

31. The method of claim 30 including the steps of monitoring changes in the amplitude data and the phase data between successive data points of the baseline data and the current data, and discarding the data for a data point if the phase data changes by more than a predetermined amount or if the amplitude data changes by more than a predetermined amount relative to a change in the rotor speed between successive data points.

32. The method of claim 30 including the steps of monitoring changes in the rotor speed between successive data points of the baseline data and the current data, and discarding the data for a data point if the rotor speed changes by more than a predetermined amount between successive data points.

33. The method of claim 28 including the step of interpolating the current data to provide current data and baseline data at matching rotor speeds.

34. The method of claim 28 wherein the data is interpolated by determining a quadratic least squares fit between successive data points of the current data.

35. A system for detecting an occurrence of a transverse crack in a rotor of a turbine-generator, comprising means for sensing the amplitude and phase of vibrations in the rotor at different speeds during a change in the speed of the rotor prior to development of a crack to provide baseline amplitude and phase data having fundamental and harmonic components, means for monitoring the amplitude and phase of the vibrations at different speeds during a subsequent change in the rotor speed to provide current amplitude and phase data having fundamental and harmonic components, means for taking a vector difference between harmonic components of the current data and the baseline data at matching rotor speeds, and means for monitoring the vector difference of the harmonic components to determine the occurrence of a crack.

36. The system of claim 35 wherein the means for providing the baseline data and the means for providing the current data each include means for discarding the data if the rotor speed changes by more than a predetermined amount between successive data points.

37. The system of claim 35 wherein the means for providing the baseline data and the means for providing the current data each include means for discarding the data if the fundamental component or a harmonic component of the phase data changes by more than a predetermined amount between successive data points.

38. The system of claim 35 wherein the baseline data and the current data include amplitude and phase data for 1Rev, 2/Rev and 3/Rev harmonics, and the means for providing the baseline data and the means for providing the current data each include means for discarding the data for a data point if the 1/Rev, 2/Rev and 3/Rev phase data changes by more than a predetermined amount between successive data points.

39. The system of claim 35 wherein the means for taking the vector difference at matching rotor speeds includes means for interpolating the current data to provide current data and baseline data at matching rotor speeds.

40. The system of claim 39 wherein the means for interpolating the data includes means for determining a quadratic least squares fit between successive data points of the current data.

41. The system of claim 35 wherein the baseline data and the current data include amplitude and phase data for 1Rev, 2/Rev and 3/Rev harmonics, and the means for providing the baseline data and the means for providing the current data each include means for discarding the data for a data point if the 1/Rev, 2/Rev and 3/Rev amplitude data changes by more than a predetermined amount relative to a change in rotor speed between successive data points.

42. A method of detecting an occurrence of a transverse crack in a rotor of a turbine-generator, comprising the steps of: sensing the amplitude and phase of vibrations in the rotor at different speeds during a change in the speed of the rotor prior to development of a crack to provide baseline amplitude and phase data having fundamental and harmonic components, monitoring the amplitude and phase of the vibrations at different speeds during a subsequent change in the rotor speed to provide current amplitude and phase data having fundamental and harmonic components, taking a vector difference between harmonic components of the current data and the baseline data at matching rotor speeds, and monitoring the vector difference of the harmonic components to determine the occurrence of a crack.

43. The method of claim 42 including the steps of monitoring the rotor speed between successive data points of the base line data and the current data and discarding the data for a data point if the rotor speed changes by more than a predetermined amount between that data point and the preceding data point.

44. The method of claim 42 including the steps of monitoring changes in the fundamental and harmonic components of the phase data between successive data points of the baseline data and the current data, and discarding the data for a data point if the fundamental component or a harmonic component of the phase data changes by more than a predetermined amount between successive data points.

45. The method of claim 42 wherein the baseline data and the current data include amplitude and phase data for 1Rev, 2/Rev and 3/Rev harmonics, and the method includes the steps of monitoring changes in the amplitude data and the phase data between successive data points of the baseline data and the current data, and discarding the data for a data point if the 1/Rev, 2/Rev and 3/Rev phase data changes by more than a predetermined amount between successive data points.

46. The method of claim 42 including the step of interpolating the current data to provide current data and baseline data at matching rotor speeds.

47. The method of claim 46 wherein the data is interpolated by determining a quadratic least squares fit between the data from successive data points of the current data.

48. The method of claim 42 wherein the baseline data and the current data include amplitude and phase data for 1Rev, 2/Rev and 3/Rev harmonics, and the method includes the steps of monitoring changes in the amplitude data and the phase data between successive data points of the baseline data and the current data, and discarding the data for a data point if the 1/Rev, 2/Rev and 3/Rev amplitude data changes by more than a predetermined amount relative to a change in rotor speed between successive data points.

* * * * *